United States Patent
Pompeo et al.

(10) Patent No.: US 7,563,748 B2
(45) Date of Patent: Jul. 21, 2009

(54) ALCOHOL ALKOXYLATE CARRIERS FOR PESTICIDE ACTIVE INGREDIENTS

(75) Inventors: Michael P. Pompeo, Mason, OH (US); Benoit Abribat, Saint Fargeau Ponthierry (FR)

(73) Assignee: Cognis IP Management GmbH, Henkelstrasse 67, Duesseldorf (DE)

( * ) Notice: Subject to any disclaimer, the term of this patent is extended or adjusted under 35 U.S.C. 154(b) by 614 days.

(21) Appl. No.: 10/848,182

(22) Filed: May 18, 2004

(65) Prior Publication Data
US 2005/0009708 A1    Jan. 13, 2005

Related U.S. Application Data

(60) Provisional application No. 60/480,786, filed on Jun. 23, 2003.

(51) Int. Cl.
*A01N 37/24* (2006.01)

(52) U.S. Cl. .................. 504/149; 424/405

(58) Field of Classification Search ............... None
See application file for complete search history.

(56) References Cited

U.S. PATENT DOCUMENTS 6,482,425 B1   11/2002   Huet et al.
6,541,516 B1 *  4/2003   Narayanan et al. ....... 514/531

FOREIGN PATENT DOCUMENTS

GB            1557804    * 12/1979
WO         WO 98/17315   *  4/1998

* cited by examiner

*Primary Examiner*—Neil Levy

(57) ABSTRACT

An agricultural pesticide composition containing: (a) from about 20 to about 99% by weight of a solvent corresponding to formula I:

$$R^1\text{-}(EO)_x\text{-}(PO)_y\text{-}R^2 \qquad (I)$$

wherein $R^1$ is an alkyl group having from about 6 to about 18 carbon atoms, x is a number from 1 to about 20, y is a number up to about 10, and $R^2$ is either —OH or —COOH; and (b) a biologically active ingredient.

3 Claims, No Drawings

ALCOHOL ALKOXYLATE CARRIERS FOR PESTICIDE ACTIVE INGREDIENTS

CROSS-REFERENCE TO RELATED APPLICATIONS

This application claims the benefit of copending provisional application Ser. No. 60/480,786 filed Jun. 23, 2003.

STATEMENT REGARDING FEDERALLY SPONSORED RESEARCH OR DEVELOPMENT

Not applicable.

BACKGROUND OF THE INVENTION

It is known that various types of pesticides such as insecticides, insect repellents, fungicides, bactericides, herbicides, and plant growth regulators may be formulated into various products for use on crops and ornamental plants, for controlling weeds, insects and the like.

These types of pesticide products may be formulated as liquids, powders or granules. Solvents, emulsifiers, dispersing agents and wetting agents are normally incorporated into such compositions in order to ensure that a uniform pesticide formulation has been prepared.

The successful employment of any pesticide depends upon its proper formulation into a preparation that can be easily diluted with water into ready-to-use mixtures for application onto a targeted pest and/or agricultural substrate with safety to the applicator, animals and plants. The preparation and use of such formulations typically necessitates making them in concentrated form. Thus, the use of auxiliary agents such as solvents, emulsifiers, wetting and dispersing agents are typically required.

Conventionally-used solvents/carriers for pesticides include, among other things, isophorone, methylisobutyl ketone and N-methyl pyrrolidone. These solvents are oftentimes either expensive, difficult to source and/or unattractive due to their inherent toxicity or regulatory status. Consequently, there exists a need in the pesticide industry to find alternatives to the currently used solvents/carrier systems.

BRIEF SUMMARY OF THE INVENTION

The present invention is directed to a pesticide composition containing:

(a) from about 20 to about 99% by weight of a solvent corresponding to formula I:

$$R^1\text{-}(EO)_x\text{-}(PO)_y\text{-}R^2 \qquad (I)$$

wherein $R^1$ is an alkyl group having from about 6 to about 18 carbon atoms, x is a number from 1 to about 20, y is a number up to about 10, and $R^2$ is either —OH or —COOH; and (b) a biologically active ingredient.

The present invention is also directed to a process for treating a target substrate involving contacting the substrate with a pesticide composition containing:

(a) from about 20 to about 99% by weight of a solvent corresponding to formula I:

$$R^1\text{-}(EO)_x\text{-}(PO)_y\text{-}R^2 \qquad (I)$$

wherein $R^1$ is an alkyl group having from about 6 to about 18 carbon atoms, x is a number from 1 to about 20, y is a number up to about 10, and $R^2$ is either —OH or —COOH; and (b) a biologically active ingredient.

BRIEF DESCRIPTION OF THE SEVERAL VIEWS OF THE DRAWING

Not applicable.

DETAILED DESCRIPTION OF THE INVENTION

Other than in the operating examples, or where otherwise indicated, all numbers expressing quantities of ingredients or reaction conditions are to be understood as being modified in all instances by the term "about".

The term agricultural substrate as used herein means a plant, a plant pest, or a combination of a plant and a plant pest. A plant pest is defined as any living stage of any insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The solvent employed by the present invention corresponds to formula I:

$$R^1\text{-}(EO)_x\text{-}(PO)_y\text{-}R^2 \qquad (I)$$

wherein $R^1$ is an alkyl group having from about 6 to about 18 carbon atoms, and preferably from about 6 to about 12 carbon atoms, x is a number from 1 to about 20, preferably from about 1 to about 6, and most preferably from about 1 to 3, y is a number up to about 10, preferably from about 1 to about 6, and most preferably from about 1 to about 2, and $R^2$ is either —OH or —COOH. A particularly preferred solvent for use in the present invention is a $C_6$-$C_{12}$ fatty alcohol having 2 moles of EO (ethylene oxide).

The biologically-active ingredients used to make agricultural pesticide compositions according to the invention are generally selected from the group consisting of insecticides, insect repellents, fungicides, bactericides, bacteriostats, herbicides, and plant growth regulators.

A particularly preferred biologically active ingredient for use in the present invention is 3,4-dichlorophenyl propanamide, i.e., propanil.

According to one embodiment of the present invention, there is thus provided a pesticide composition containing: (a) from about 20 to about 99% by weight, preferably from about 20 to about 80% by weight, and most preferably from about 25 to about 55% by weight of a $C_6$-$C_{18}$ fatty alcohol and/or fatty acid alkoxylated with from 1 to about 20 moles of ethylene oxide and up to about 10 moles of propylene oxide; and (b) from about 1 to about 80% by weight, preferably from about 10 to about 60% by weight, and most preferably from about 38 to about 50% by weight of a biologically-active ingredient, all weights being based on the weight of the composition.

The pesticide composition of the present invention may also include various types of auxiliaries/adjuvants which serve to further enhance the performance capabilities of the pesticide composition.

Suitable nonionic surfactants for use in the present invention include alkoxylated fatty alcohols, alkoxylated fatty acids, alkoxylated fatty ethers, alkoxylated fatty amides, ethoxylated seed oils, ethoxylated mineral oils, nonylphenol ethoxylates, alkoxylated alkyl phenols, ethoxylated glycerides, castor oil ethoxylates, and mixtures thereof.

The anionic surfactants that can be used in the compositions according to the invention are selected from the group consisting of an ethoxylated partial phosphate ester, an alkyl sulfate and, an alkyl ether sulfate, a branched alkyl benzene sulfonate, a linear alkyl benzene sulfonate and an alpha olefin sulfonate.

The alkyl sulfates that can be used in the compositions according to the invention are those wherein the alkyl group has from about 6 to about 22 carbon atoms. The alkyl ether sulfates that can be used in the compositions according to the invention are those wherein the alkyl group has from about 6 to about 22 carbon atoms. The branched alkyl benzene sulfonates that can be used in the compositions according to the invention are those wherein the alkyl group can be branched and has from about 6 to about 22 carbon atoms. The linear alkyl benzene sulfonates that can be used in the compositions according to the invention are those wherein the alkyl group is an essentially unbranched alkyl group having from about 6 to about 22 carbon atoms. The alpha olefin sulfonates that can be used in the compositions according to the invention are those wherein the alkyl group has from about 6 to about 22 carbon atoms.

Auxilliary components may also be added to the adjuvant composition of the present invention, in order to further enhance the properties thereof. Examples thereof include, but are not limited to, water-soluble silicone surfactants, oil-soluble silicone surfactants, cationic surfactants, amphoteric surfactants, and the like.

Cationic surfactants which may be employed include, but are not limited to, ethoxylated amines such as ethoxylated tallow amine.

Amphoteric surfactants which may be employed include, but are not limited to, amino acids and their derivatives, amino acid salts, imidazolinium derivatives, alkyl betaines and amidopropyl anologues.

What is claimed is:

1. A pesticidal concentrate composition comprising:
   (a) from about 20 to about 99% by weight of a solvent corresponding to formula I:

$$R^1\text{-}(EO)_x\text{-}(PO)_y\text{-}R^2 \qquad (I)$$

wherein $R^1$ is an alkyl group having from about 6 to about 18 carbon atoms, x is a number from 1 to about 20, y is a number up to about 10, $R^2$ is either OH or COCH, (EO) is an ethylene oxide residue and (PO) is a propylene oxide residue; and
   (b) a pesticidally active ingredient comprising 3,4-dichlorophenyl propanamide.

2. A process for treating a target substrate comprising contacting the substrate with a diluted pesticide concentrate composition comprising:
   (a) from about 20 to about 99% by weight of a solvent corresponding to formula I:

$$R^1\text{-}(EO)_x\text{-}(PO)_y\text{-}R^2 \qquad (I)$$

wherein $R^1$ is an alkyl grourp having from about 6 to about 18 carbon atoms, x is a number from 1 to about 20, y is a number up to about 10, $R^2$ is either —OH or —COOH, (EO) is an ethylene oxide residue and (PO) is a propylene oxide residue; and
   (b) a pesticidally active ingredient comprising 3,4-dichlorophenyl propanamide.

3. The process of claim 2 wherein the solvent comprises a $C_{6\text{-}12}$ fatty alcohol ethoxylate, wherein, x is 2.

* * * * *